United States Patent
Yuan et al.

(10) Patent No.: US 10,973,885 B2
(45) Date of Patent: Apr. 13, 2021

(54) ORAL CARE COMPOSITIONS

(71) Applicant: Colgate-Palmolive Company, New York, NY (US)

(72) Inventors: Shaotang Yuan, East Brunswick, NJ (US); Paloma Pimenta, Staten Island, NY (US); Dennis Ontumi, Easton, PA (US); Jennifer Gronlund, Flemington, NJ (US); Robert Dicosimo, Chadds Ford, PA (US); Sharon Haynie, Philadelphia, PA (US); Mark S. Payne, Wilmington, DE (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/719,889

(22) Filed: Dec. 18, 2019

(65) Prior Publication Data

US 2020/0206320 A1 Jul. 2, 2020

Related U.S. Application Data

(60) Provisional application No. 62/785,564, filed on Dec. 27, 2018.

(51) Int. Cl.

| | | |
|---|---|---|
| *A61K 38/46* | (2006.01) |
| *A61K 31/19* | (2006.01) |
| *A61K 31/194* | (2006.01) |
| *A61K 33/40* | (2006.01) |
| *A61K 38/50* | (2006.01) |
| *A61K 47/02* | (2006.01) |
| *A61K 47/18* | (2017.01) |
| *A61K 47/20* | (2006.01) |
| *A61K 47/32* | (2006.01) |
| *A61K 47/34* | (2017.01) |
| *A61Q 11/00* | (2006.01) |
| *C12N 9/14* | (2006.01) |
| *C12N 9/18* | (2006.01) |
| *C12N 9/80* | (2006.01) |

(52) U.S. Cl.
CPC .............. *A61K 38/46* (2013.01); *A61K 31/19* (2013.01); *A61K 31/194* (2013.01); *A61K 33/40* (2013.01); *A61K 38/465* (2013.01); *A61K 38/50* (2013.01); *A61K 47/02* (2013.01); *A61K 47/186* (2013.01); *A61K 47/20* (2013.01); *A61K 47/32* (2013.01); *A61K 47/34* (2013.01); *A61Q 11/00* (2013.01); *C12N 9/14* (2013.01); *C12N 9/18* (2013.01); *C12N 9/80* (2013.01)

(58) Field of Classification Search
CPC .............. A61Q 11/00; A61K 8/66; A61K 8/22
USPC ................................. 424/49, 50, 53
See application file for complete search history.

(56) References Cited

U.S. PATENT DOCUMENTS

| | | |
|---|---|---|
| 6,221,341 B1 | 4/2001 | Montgomery |
| 7,189,385 B2 | 3/2007 | Montgomery |
| 8,158,686 B2 | 4/2012 | Bouillo et al. |
| 8,389,254 B2 | 3/2013 | Payne |
| 8,540,971 B2 | 9/2013 | Prencipe |
| 9,884,000 B2 | 2/2018 | Boyd et al. |
| 9,974,634 B2 | 5/2018 | Maloney et al. |
| 10,098,824 B2 | 10/2018 | Boyd et al. |
| 10,413,500 B2 | 9/2019 | Gronlund et al. |
| 10,426,719 B2 | 10/2019 | Yuan et al. |
| 2005/0036956 A1 | 2/2005 | Prencipe |
| 2006/0024246 A1 | 2/2006 | Ibrahim |
| 2007/0071695 A1 | 3/2007 | Chopra et al. |
| 2007/0071696 A1 | 3/2007 | Qin et al. |
| 2009/0311198 A1* | 12/2009 | Concar ............... A61K 8/66 424/50 |
| 2012/0244091 A1 | 9/2012 | Prencipe |
| 2018/0168973 A1 | 6/2018 | Hassan et al. |

FOREIGN PATENT DOCUMENTS

| | | |
|---|---|---|
| KR | 101197673 B1 | 11/2012 |
| WO | 2012/087970 | 6/2012 |
| WO | 2013/148190 | 10/2013 |

OTHER PUBLICATIONS

International Search Report and the Written Opinion of the International Searching Authority issued in International Application PCT/US2019/067282 dated Apr. 14, 2020.
International Search Report and Written Opinion of the International Searching Authority in International Application No. PCT/US2017/065744, dated Mar. 5, 2018.

\* cited by examiner

*Primary Examiner* — Walter E Webb

(57) ABSTRACT

An oral care composition, including a catalyzing enzyme and an anhydrous matrix configured to at least partially stabilize the catalyzing enzyme, wherein the anhydrous matrix includes a source of hydrogen peroxide, an acyl donor, a non-aqueous anhydrous liquid, and a surfactant mixture including sodium lauryl sulfate (SLS), Betaine, and a poloxamer.

18 Claims, No Drawings

Specification includes a Sequence Listing.

SEQUENCE LISTING

<160> NUMBER OF SEQ ID NOS: 3

<210> SEQ ID NO 1
<211> LENGTH: 325
<212> TYPE: PRT
<213> ORGANISM: Thermotoga maritima

<400> SEQUENCE: 1

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175
```

```
Val Asp Gln Glu Arg Ile Val Ile Ala Gly Gly Ser Gln Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Ser Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 2
<211> LENGTH: 318
<212> TYPE: PRT
<213> ORGANISM: Bacillus subtilis

<400> SEQUENCE: 2

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Leu His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
```

```
                    210                 215                 220
Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
                260                 265                 270

Pro Pro Ser Thr Val Phe Ala Ala Tyr Asn His Leu Glu Thr Glu Lys
            275                 280                 285

Glu Leu Lys Val Tyr Arg Tyr Phe Gly His Glu Tyr Ile Pro Ala Phe
            290                 295                 300

Gln Thr Glu Lys Leu Ala Phe Phe Lys Gln His Leu Lys Gly
305                 310                 315

<210> SEQ ID NO 3
<211> LENGTH: 5
<212> TYPE: PRT
<213> ORGANISM: Artificial Sequence
<220> FEATURE:
<223> OTHER INFORMATION: Motif in CE-7 family
<220> FEATURE:
<221> NAME/KEY: misc_feature
<222> LOCATION: (2)..(2)
<223> OTHER INFORMATION: Xaa is any amino acid residue

<400> SEQUENCE: 3

Gly Xaa Ser Gln Gly
1               5
```

ORAL CARE COMPOSITIONS

SEQUENCE LISTING

The instant application contains a Sequence Listing which has been submitted electronically in ASCII format and is hereby incorporated by reference in its entirety. Said ASCII copy, created on Nov. 28, 2018, is named 12179-00-OC_ST25.txt, and is 7000 bytes in size.

BACKGROUND

Oral care compositions (e.g., toothpastes, whitening gels, etc.) incorporating whitening agents are commonly used to whiten teeth. Peroxides, such as hydrogen peroxide, are one of the most common teeth whitening agents. In addition, in order to improve teeth whitening efficacy, some oral care compositions include a combination of teeth whitening agents or include additional ingredients configured to boost an effect of the teeth whitening agents. For example, some oral care compositions may include catalyzing enzymes and/or acyl donors configured to create teeth whitening enhancers, such as peroxyacid or peracetic acid, in the presence of hydrogen peroxide.

However, whitening agents having relatively increased reactivity are often unstable and subject to degradation. For example, hydrogen peroxide is an unstable molecule that is prone to decomposition, especially in aqueous environments. Similarly, catalyzing enzymes may be denatured or destabilized in the presence of certain ingredients commonly found in oral care compositions, such as specific detergents or surfactants.

Accordingly, it would be useful to develop oral care compositions incorporating whitening agents with improved stability and efficacy.

BRIEF SUMMARY

This summary is intended merely to introduce a simplified summary of some aspects of one or more implementations of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition, including a catalyzing enzyme; and an anhydrous matrix configured to at least partially stabilize the catalyzing enzyme, wherein the anhydrous matrix includes a source of hydrogen peroxide; an acyl donor; a non-aqueous anhydrous liquid; and a surfactant mixture, wherein the surfactant mixture includes sodium lauryl sulfate (SLS), Betaine, and a poloxamer having a molecular weight of 5,000 or more Daltons.

The poloxamer in the surfactant mixture may be at least one of an ethylene oxide-propylene oxide polymer or a polyethylene glycol/polypropylene glycol (PEG/PPG) copolymer, and wherein the betaine may be anhydrous cocamidopropyl betaine.

The surfactant mixture may include from about 0.5 weight % to about 5.0 weight % SLS, based on a total weight of the oral care composition; from about 0.01 weight % to about 5.0 weight % anhydrous cocamidopropyl betaine, based on the total weight of the oral care composition; and from about 0.5 weight % to about 20.0 weight % of the PEG/PPG copolymer, based on the total weight of the oral care composition.

The surfactant mixture may include from about 0.5 weight % to about 3.0 weight % SLS, based on a total weight of the oral care composition; from about 0.5 weight % to about 3.0 weight % anhydrous cocamidopropyl betaine, based on the total weight of the oral care composition; and from about 2.0 weight % to about 10.0 weight % of the PEG/PPG copolymer, based on the total weight of the oral care composition.

The surfactant mixture may consist essentially of from about 1.0 weight % to about 2.0 weight % SLS, based on a total weight of the oral care composition; from about 1.0 weight % to about 2.0 weight % anhydrous cocamidopropyl betaine, based on the total weight of the oral care composition; and from about 3.0 weight % to about 8.0 weight % of the PEG/PPG copolymer, based on the total weight of the oral care composition.

The catalyzing enzyme may have perhydrolytic activity and may be capable of generating peracetic acid via enzyme-catalyzed perhydrolysis.

The source of hydrogen peroxide may be a cross-linked polyvinylpyrrolidone (PVP) hydrogen peroxide complex.

The anhydrous matrix may be substantially free of water.

The acyl donor may be one or more of a $C_{2-18}$ carboxylic acid, a hydrolysable ester, and mixtures thereof.

The acyl donor may be triacetin.

The oral care composition may further include a thickener, wherein the thickener includes a cross-linked polyvinylpyrrolidone.

The thickener may further include a silica thickener.

The catalyzing enzyme may include a CE-7 signature motif that aligns with SEQ ID NO: 2, the CE-7 signature motif comprising a) an RGQ motif at positions corresponding to positions 118-120 of SEQ ID NO: 2; b) a GXSQG (SEQ ID NO: 3) motif at positions corresponding to positions 179-183 of SEQ ID NO: 2 and an HE motif at positions corresponding to positions 298-299 of SEQ ID NO:2.

The catalyzing enzyme may include an amino acid sequence comprising a CE-7 signature motif and having at least 80% amino acid sequence identity to SEQ ID NO:1.

The non-aqueous anhydrous liquid may include a polyethylene oxide-polypropylene oxide block copolymer having a molecular weight of 5,000 Daltons or less.

The non-aqueous anhydrous liquid may include poly (ethylene glycol)-block-poly(propylene glycol)-block-poly (ethylene glycol).

The catalyzing enzyme may include SEQ ID NO:1.

The foregoing and/or other aspects and utilities embodied in the present disclosure may also be achieved by providing a method for whitening teeth, including contacting the oral care composition of claim 1 with water on a surface of the teeth, wherein contacting the oral care composition with water on the surface of the teeth generates peracetic acid.

BRIEF DESCRIPTION OF BIOLOGICAL SEQUENCES

SEQ ID NO: 1 is the amino acid sequence of *Thermotoga maritima* C277S variant perhydrolase (also referred to herein as EZ-1).

SEQ ID NO: 2 is the amino acid sequence of a cephalosporin C deacetylase from *Bacillus sublilis* ATCC® 31954™.

SEQ ID NO: 3 is a motif, GXSQG, wherein X is any amino acid residue. This motif is shared among members of the carbohydrate esterase family 7 (CE-7 family).

DETAILED DESCRIPTION

Reference will now be made in detail to the various implementations in the present disclosure, examples of which may be illustrated in any accompanying drawings and FIGURES. The various implementations are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the various implementations.

Throughout the specification and claims, the following terms take the meanings explicitly associated herein, unless the context clearly dictates otherwise. Phrases such as "in an implementation," "in certain implementations," and "in some implementations" as used herein do not necessarily refer to the same implementation(s), though they may. Furthermore, the phrases "in another implementation" and "in some other implementations" as used herein do not necessarily refer to a different implementation, although they may. As described below, various implementations may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes implementations containing A, B, or C, multiple examples of A, B, or C, or combinations of A/B, A/C, B/C, A/B/B/ BB/C, AB/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, component, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5% to 6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Unless otherwise specified, all percentages and amounts expressed herein and elsewhere in the specification should be understood to refer to percentages by weight. The amounts given are based on the active weight of the material.

With regard to procedures, methods, techniques, and workflows that are in accordance with some implementations, some operations in the procedures, methods, techniques, and workflows disclosed herein may be combined and/or the order of some operations may be changed.

As described in the present disclosure, the inventors have surprisingly and unexpectedly discovered an oral care composition including a variety of whitening agents with improved stability and efficacy. In particular, the inventors have developed an anhydrous matrix capable of stabilizing sources of hydrogen peroxide, catalyzing enzymes, and acyl donors that can be used a base for oral care compositions. For example, the catalyzing enzymes may be contacted, mixed, commingled, agglomerated, or otherwise combined within the anhydrous matrix, which may include the sources of hydrogen peroxide, the acyl donors, the non-aqueous anhydrous liquids, a surfactant mixture, and/or thickeners. The anhydrous matrix may be mixed or maintained as a single homogenous phase. Said anhydrous matrix can then be used as a base for a variety of oral care compositions (e.g., toothpaste, whitening gel, rinse-off or leave-on pastes or gels, etc.).

For example, the anhydrous matrix may include one or more sources of hydrogen peroxide, one or more acyl donors, and a surfactant mixture. The anhydrous matrix may also include one or more catalyzing enzymes. In some implementations, the anhydrous matrix may also include one or more non-aqueous anhydrous liquids and/or one or more thickeners.

As used herein, the term "anhydrous" refers to compositions that may be free or substantially free of water. For example, the anhydrous matrix may be substantially free of water before use as an oral care composition. Similarly, the oral care composition may be substantially free of water. As used herein, the terms "free" or "substantially free" of water may refer to an oral care composition that contains less than 10 weight %, less than 5 weight %, less than 3 weight %, less than 1 weight %, less than 0.1 weight %, less than 0.05 weight %, less than 0.01 weight %, less than 0.005 weight %, and/or less than 0.001 weight % water based on the total weight of the oral care composition. For example, in one implementation, the oral care composition includes 2 weight % or less water. In another implementation, the oral care composition has no free water.

All ingredients used in the oral care compositions described herein should be orally acceptable. "Orally acceptable" means an ingredient which is present in the oral care compositions as described in an amount and form which does not render said oral care composition unsafe, unpalatable, or otherwise unsuitable for use in the oral cavity.

The anhydrous matrix, and/or the resultant oral care composition, may include one or more sources of hydrogen peroxide. The sources of hydrogen peroxide may be configured to release hydrogen peroxide when contacted with water.

The sources of hydrogen peroxide may include, but are not limited to, hydrogen peroxide, urea peroxide, calcium peroxide, a cross-linked polyvinylpyrrolidone (PVP) hydrogen peroxide complex, a polyvinylpyrrolidone (PVP) hydrogen peroxide complex, sodium percarbonate, and the like, and combinations thereof. The sources of hydrogen peroxide may also be or include, but are not limited to, PEROXYDONE™ XL 10, which is commercially available from Ashland Inc. of Covington, Ky. In one implementation, the sources of peroxide include a crosslinked polyvinylpyrrolidone complexed with hydrogen peroxide (PVP-$H_2O_2$ or PVP-HP).

In at least one implementation, the one or more sources of hydrogen peroxide may be or include one or more peroxide complexes. The peroxide complex may include a peroxide component and a porous cross-linked polymer. As used herein, a "peroxide component" may be or include any oxidizing compound including a bivalent oxygen-oxygen group. Peroxide components may be or include, but are not limited to, peroxides and hydroperoxides, such as hydrogen peroxide, peroxides of alkali and alkaline earth metals, organic peroxy compounds, peroxy acids, pharmaceutically-acceptable salts thereof, and the like, and combinations or mixtures thereof. Peroxides of alkali and alkaline earth metals may include, but are not limited to, lithium peroxide, potassium peroxide, sodium peroxide, magnesium peroxide, calcium peroxide, barium peroxide, and the like, and combinations or mixtures thereof. Organic peroxy compounds may include, but are not limited to, carbamide peroxide (e.g., urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate, and the like, and combinations and mixtures thereof. Peroxy acids and their salts may include, but are not limited to, organic peroxy acids, such as alkyl peroxy acids, monoperoxyphthalate, and the like, and combinations or mixtures thereof. Peroxy acids and their salts may also be or include, but are not limited to, inorganic peroxy acid salts, such as percarbonate and perborate salts of alkali and alkaline earth metals (e.g., lithium, potassium, sodium, magnesium, calcium and barium), and the like, and combinations or mixtures thereof. In various implementations, the peroxide component includes hydrogen peroxide, urea peroxide, sodium percarbonate, and combinations or mixtures thereof. In another implementation, the peroxide component includes hydrogen peroxide.

In at least one implementation, the porous cross-linked polymer of the peroxide complex may be or include, but is not limited to, an N-vinyl heterocyclic polymer. The porous cross-linked polymer may be configured to adsorb, complex with, or otherwise retain the peroxide component. The porous cross-linked polymer may be configured to retain the peroxide component until release is initiated. For example, the porous cross-linked polymer may retain the peroxide component until contacted with water. In at least one implementation, the peroxide complex may be a particulate, such as a polymer particulate. The porous cross-linked polymer of the peroxide complex may control the release of the peroxide component from the peroxide complex. For example, the porous cross-linked polymer may hinder control (e.g., hasten or slow) the release of the peroxide component from the polymer particulate.

In at least one implementation, the N-vinyl heterocyclic polymer may be derived from a N-heterocyclic vinyl monomer, typically including N-vinyl heterocyclic monomers having from about 3 to about 7 atoms in a heterocyclic ring, including a carbonyl carbon atom and a nitrogen heteroatom containing a vinyl group. In a typical implementation, the ring contains five or six atoms including heteroatoms such as sulfur or oxygen, and may be substituted or unsubstituted.

In at least one implementation, the porous cross-linked polymer may be or include, but is not limited to, KOLLIDONE® and/or LUVICROSS®, both of which are commercially available from BASF of Mount Olive, N.J., PVP K-Series and/or POVIDONE™ K-30, which are commercially available from AAA International Corp. of Downers Grove, Ill., PVP K-30 USP24, PVP VA-64, PVP K-17, and PVP K-90, which are commercially available from Peakchem, Hangzhou, China, and POLYPLASDONE® INF-10, which is commercially available from ISP Corporation of Wayne, N.J.

The amount of the peroxide component present in the peroxide complex may be from about 0.1 weight % to about 40 weight % based on a total weight of the peroxide complex. For example, the amount of the peroxide component present in the peroxide complex may be about 1 weight % to about 30 weight %, about 5 weight % to about 20 weight %, about 8 weight % to about 15 weight %, or about 10 weight % to about 13 weight %, based on a total weight of the peroxide complex. In a typical implementation, the source of the hydrogen peroxide includes a complex of hydrogen peroxide adsorbed into a cross-linked polyvinylpyrrolidone (PVP). For example, the source of the hydrogen peroxide includes PEROXYDONE™ XL 10 and/or PEROXYDONE™ K-30, both of which are commercially available from Ashland Inc. of Covington, Ky. In a typical implementation, the source of hydrogen peroxide is PEROXYDONE™ XL 10, which is 18% $H_2O_2$, and the oral care composition includes an amount of the source of hydrogen peroxide configured to provide about 0.1 weight % hydrogen peroxide, based on a total weight of the oral care composition.

The amount or concentration of the source of hydrogen peroxide in the oral care composition may vary widely. In one implementation, the amount of the source of hydrogen peroxide may be from about 0.1 weight % to about 50 weight %, based on a total weight of the oral care composition. For example, the oral care composition may include from about 0.1 weight % to about 40 weight % source of hydrogen peroxide or from about 0.1 weight % to about 35 weight % source of hydrogen peroxide.

The amount of hydrogen peroxide in the oral care composition is from about 0.05 weight % to about 35 weight %. For example, the amount of the source of hydrogen peroxide in the oral care composition may be configured to provide from about 0.1 weight % to about 20 weight % or 0.1 weight % to about 10 weight % hydrogen peroxide to the oral care composition. In one implementation, the amount of the source of hydrogen peroxide is configured to provide about 0.1 weight % hydrogen peroxide to the oral care composition. In other implementations, the oral care composition includes 2 weight % or less, 1.5 weight % or less, 1.0 weight % or less, 0.5 weight % or less, 0.4 weight % or less, 0.3 weight % or less, 0.2 weight % or less, 0.1 weight % or less, or 0.05 weight % or less hydrogen peroxide.

The anhydrous matrix, and/or the resultant oral care composition, may include one or more acyl donors. The acyl donors may be or include, but are not limited to, $C_{2-18}$ carboxylic acids, including lower linear or branched alkyl carboxylic acids, hydrolysable esters of $C_{2-18}$ carboxylic acids, and the like, and mixtures or combinations thereof. In at least one example, the $C_{2-18}$ carboxylic acids may be unsubstituted. In another example, the $C_{2-18}$ carboxylic acids may be substituted with a hydroxyl and/or a $C_{1-4}$ alkoxy group. In at least one implementation, one or more of the acyl donors may be an ester represented by Formula (1) below:

  (1)

  (2)

where X is an ester group represented by Formula (2), $R_5$ is a $C_{1-6}$ linear, branched, or cyclic hydrocarbyl moiety, a five-member cyclic heteroaromatic moiety, or a six-member cyclic aromatic or heteroaromatic moiety, optionally substituted with hydroxyl groups, where each individually carbon atom in $R_5$ includes no more than one hydroxyl group, no more than one ester group, no more than one ester group or carboxylic acid group, where $R_5$ optionally includes one or more ether linkages, where m is an integer from 1 to the number of carbon atoms in $R_5$, and where the esters have a solubility in water of at least 5 ppm at 25° C.; where $R_6$ is a $C_1$ to $C_7$ linear, branched or cyclic hydrocarbyl moiety, optionally substituted with a hydroxyl group or $C_1$ to $C_4$ alkoxy group, wherein $R_6$ optionally includes one or more ether linkages where $R_6$ is $C_2$ to $C_7$.

In another implementation, one or more of the acyl donors may be a glyceride represented by Formula (3):

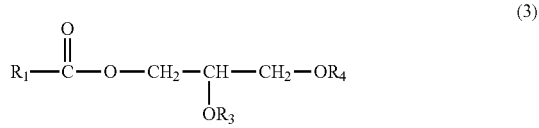  (3)

where $R_1$ is a $C_{1-7}$ straight or branch chain alkyl, optionally substituted with a hydroxyl or a $C_{1-4}$ alkoxy group, and $R_3$ and $R_4$ are individually an H or an $R_1C(O)$.

In another implementation, one or more of the acyl donors may be an ester represented by Formula (4):

  (4)

where $R_1$ is a $C_{1-7}$ straight or branch chain alkyl, optionally substituted with a hydroxyl or a $C_{1-4}$ alkoxy group, $R_2$ is a $C_{1-10}$ straight or branch chain alkyl, alkenyl, alkynyl, aryl, alkylaryl, alkylheteroaryl, heteroaryl, $(CH_2CH_2O)_n$, or $(CH_2CH(CH_3)\text{—}O)_nH$, and n is an integer from 1 to 10.

In yet another implementation, one or more of the acyl donors may be an acetylated saccharide. Illustrated acetylated saccharides may be or include, but is not limited to, acetylated monosaccharides, acetylated disaccharides, acetylated polysaccharide, and the like, and combinations thereof.

In at least one implementation, one or more of the acyl donors may be or include, but are not limited to, $C_{2-18}$ carboxylic acids, $C_{2-6}$ carboxylic acids (e.g., acetic acid), including lower linear or branched alkyl carboxylic acids, optionally substituted with hydroxy and/or $C_{1-4}$ alkoxy groups, hydrolysable and acceptable esters thereof (e.g., mono-, di-, and tri-glycerides, and acylated saccharides), and mixtures thereof. In at least one example, the acyl donors may be or include, but are not limited to 1,2,3-triacetoxypropane or triacetin or glycerin triacetate, acylated saccharides, and the like, and combinations thereof. In at least one implementation, the acyl donor or ester may have a water solubility of at least 5 ppm at 25° C. In a typical implementation, the acyl donor is 1,2,3-triacetoxypropane or triacetin (TA).

In at least one implementation, the acyl donors may be or include, but are not limited to, one or more acylated saccharides selected from acylated mono-, di-, and polysaccharides. In another implementation, the acylated saccharides are selected from acetylated xylan, fragments of acetylated xylan, acetylated xylose (e.g., xylose tetraacetate), acetylated glucose (e.g., α-D-glucose pentaacetate, β-D-glucose pentaacetate, 1-thio-β-D-glucose-2,3,4,6-tetraacetate), β-D-galactose pentaacetate, sorbitol hexaacetate, sucrose octaacetate, β-D-ribofuranose-1,2,3,5-tetraacetate, β-D-ribofuranose-1,2,3,4-tetraacetate, tri-O-acetyl-D-galactal, tri-O-acetyl-D-glucal, β-D-xylofuranose tetraacetate, β-D-glucopyranose pentaacetate, β-D-glucopyranose-1,2,3,4-tetraacetate, β-D-glucopyranose-2,3,4,6-tetraacetate, 2-acetamido-2-deoxy-1,3,4,6-tetracetyl-β-D-glucopyranose, 2-acetamido-2-deoxy-3,4,6-triacetyl-1-chloride-α-D-glucopyranose, β-D-mannopyranose pentaacetate, and acetylated cellulose. In a typical implementation, the acetylated saccharide is selected from β-D-ribofuranose-1,2,3,5-tetraacetate, tri-O-acetyl-D-galactal, tri-O-acetyl-D-glucal, sucrose octaacetate, and acetylated cellulose. In another implementation, the acyl donors may include 5-acetoxymethyl-2-furaldehyde, 3,4-diacetoxy-1-butene, 4-acetoxybenezoic acid, vanillin acetate, propylene glycol methyl ether acetate, methyl lactate, ethyl lactate, methyl glycolate, ethyl glycolate, methyl methoxyacetate, ethyl methoxyacetate, methyl 3-hydroxybutyrate, ethyl 3-hydroxybutyrate, and triethyl 2-acetyl citrate.

In yet another implementation, the acyl donors are selected from monoacetin, diacetin, triacetin, monopropionin, dipropionin, tripropionin, monobutyrin, dibutyrin, tributyrin, glucose pentaacetate, xylose tetraacetate, acetylated xylan, acetylated xylan fragments, β-D-ribofuranose-1,2,3,5-tetraacetate, tri-O-acetyl-D-galactal, tri-O-acetyl-D-glucal, monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,5-pentanediol, 1,6-pentanediol, 1,2-hexanediol, 2,5-hexanediol, 1,6-hexanediol, and mixtures thereof. In a further implementation, the acyl donor is propylene glycol diacetate (PGDA), ethylene glycol diacetate (EGDA), or a mixture thereof. In yet another implementation, the acyl donors are selected from monoacetin, diacetin, triacetin, monopropionin, dipropionin, tripropionin, monobutyrin, dibutyrin, and tributyrin. In yet another aspect, the acyl donor is selected from diacetin and triacetin.

The one or more acyl donors may be or include any compound or material configured to react with any one or more of the sources of hydrogen peroxide, or the hydrogen peroxide thereof, and/or any one or more of the catalyzing enzymes to form a whitening enhancer, such as peracetic acid.

The amount or concentration of the acyl donor may vary widely. In at least one implementation, the amount of the acyl donor may be at least partially determined by a target or desired concentration of peroxyacid or peracetic acid to be generated via enzyme-catalyzed perhydrolysis. For example, the target or desired concentration of peroxyacid or peracetic acid to be generated via enzyme-catalyzed perhydrolysis may be less than or equal to about 2,000 ppm, and the amount of the acyl donor present in the oral care composition may be greater than or equal to 0.05 weight % and less than or equal to 40 weight % based on a total weight of the oral care composition. For example, the amount of the acyl donor present in the oral care composition may be from about 0.05 weight %, about 5 weight %, about 10 weight %, about 15 weight %, about 20 weight %, or about 25 weight % to about 30 weight %, about 35 weight %, or about 40 weight %. In another implementation, the amount of the acyl donor present in the oral care composition may be less than 20 weight %. For example, the amount of the acyl donor present in the oral care composition may be less than 10 weight %, less than 9.5 weight %, less than 9.0 weight %, less than 8.5 weight %, less than 8.0 weight %, less than 7.5 weight %, less than 7.0 weight %, less than 6.5 weight %, less than 6.0 weight %, less than 5.5 weight %, less than 5.0 weight %, less than 4.5 weight %, less than 4.0 weight %, less than 3.5 weight %, less than 3.0 weight %, less than 2.5 weight %, less than 2.0 weight %, less than 1.5 weight %, less than 1.0 weight %, less than 0.9 weight %, less than 0.8 weight %, less than 0.7 weight %, less than 0.6 weight %, less than 0.5 weight %, less than 0.4 weight %, less than 0.3 weight %, less than 0.2 weight %, or less than 0.1 weight %.

In at least one implementation, the amount of the acyl donor present in the oral care composition may be from about 2 weight % to about 20 weight % based on a total weight of the oral care composition. For example, the amount of the acyl donor present in the oral care composition may be from about 10 weight %, about 11 weight %, about 12 weight %, about 13 weight %, or about 14 weight % to about 16 weight %, about 17 weight %, about 18 weight %, about 19 weight %, or about 20 weight %. In another example, the amount of the acyl donor present in the oral care composition may be from about 10 weight % to about 20 weight %, about 11 weight % to about 19 weight %, about 12 weight % to about 18 weight %, about 13 weight % to about 17 weight %, about 14 weight % to about 16 weight %, or about 17.5 weight %. In a typical implementation, the amount of the acyl donor present in the oral care composition is about 15 weight %. In other implementations, the amount of acyl donor is 12.23 weight % or 13 weight %, based on the total weight of the oral care composition.

The anhydrous matrix, and/or the resultant oral care composition, includes a surfactant mixture. In some implementations, the surfactant mixture enhances the stability of the composition, helps clean the oral cavity surfaces through detergency, and provide foam upon agitation, e.g., during brushing with an oral care composition of the disclosure. The surfactant mixture further increases a whitening action by thoroughly dispersing the anhydrous matrix or the whitening enhancer thereof throughout the oral cavity. In various implementations, the surfactants of the surfactant mixture function as a surface active agent, emulsifier, and/or foam modulator.

While not intending to be bound to any particular theory, the inventors believe that the surfactant mixture improves the stability and efficacy of the oral care composition by preserving the integrity of the ingredients required to produce peracetic acid. For example, traditional non-aqueous whitening product commonly use SLS in a one-surfactant system. However, SLS is known to denature enzymes, and thus, would degrade the production of enzyme-based peracetic acid production. In contrast, the inventors have surprisingly discovered a surfactant mixture that prevents enzyme denaturing while maintaining formulation stability and foam profile.

In one implementation, the surfactant mixture includes sodium lauryl sulfate (SLS), betaine, and a poloxamer.

In some implementations, the poloxamer is a non-ionic surfactant composed of blocks of polyethylene glycol (PEG) and polypropylene glycol (PPG). For example, nonionic tri-block copolymers composed of a central hydrophobic chain of polyoxypropylene (poly(propylene oxide)) flanked by two hydrophilic chains of polyoxyethylene (poly(ethylene oxide)). In one implementation, the poloxamer is an ethylene oxide-propylene oxide polymer. The ethylene oxide-propylene oxide polymer may be a PEG/PPG copolymer. For example, the ethylene oxide-propylene oxide polymer may be a poloxamer surfactant, such as Pluracare L1220 available commercially from BASF of Mount Olive, N.J.). In one implementation, the oral care composition includes from about 0.5 weight % to about 5.0 weight % SLS, from about 0.01 weight % to about 5.0 weight % betaine, and from about 0.5 weight % to about 20.0 weight % poloxamer.

In some implementations, the poloxamer has a high molecular weight. For example, the poloxamer may have a molecular weight of 5,000 Daltons or more, 6,000 Daltons or more, 7,000 Daltons or more, or 8,000 Daltons or more. In one implementation, the poloxamer has a molecular weight from about 8,500 Daltons to about 12,500 Daltons.

In some implementations, the betaine is provided as an anhydrous powder. For example, in some implementations, the oral care composition does not include aqueous or water based betaine. In one implementation, the betaine includes anhydrous cocamidopropyl betaine.

In other implementations, the surfactant mixture consists essentially of sodium lauryl sulfate (SLS), anhydrous cocamidopropyl betaine, and an ethylene oxide-propylene oxide polymer.

In some implementations, the oral care composition includes from about 0.5 weight % to about 5.0 weight % SLS, from about 0.01 weight % to about 5.0 weight % anhydrous cocamidopropyl betaine, and from about 0.5 weight % to about 20.0 weight % of the ethylene oxide-propylene oxide polymer. In some implementations, the oral care composition includes from about 0.5 weight % to about 3.0 weight % SLS, from about 0.5 weight % to about 3.0 weight % anhydrous cocamidopropyl betaine, and from about 2.0 weight % to about 10.0 weight % of the ethylene oxide-propylene oxide polymer. In other implementations, the oral care composition includes from about 1.0 weight % to about 2.0 weight % SLS, from about 1.0 weight % to about 2.0 weight % anhydrous cocamidopropyl betaine, and from about 3.0 weight % to about 8.0 weight % of the ethylene oxide-propylene oxide polymer.

In some implementations, the oral care composition has a 1:1 ratio of SLS to betaine. For example, the oral care composition may include a 1:1 ratio of SLS to anhydrous cocamidopropyl betaine. In other implementations, the oral care composition has a poloxamer concentration at least 2× higher than the SLS content. For example, the oral care composition may include at least 2× more ethylene oxide-propylene oxide polymer than SLS or the ratio of SLS to ethylene oxide-propylene oxide polymer is 1:2 or higher.

As described above, certain catalyzing enzymes may be denatured or destabilized in the presence of certain surfactants, limiting their ability to generate whitening enhancers, such as peroxyacid or peracetic acid. For example, high levels of SLS are associated with low levels of stability for catalyzing enzymes in oral care compositions over time. In certain cases, the stability of the catalyzing enzymes is measured in terms of the generation of whitening enhancers, such as peracetic acid (PAA). However, SLS is an important surfactant for proper foam generation and cleaning in oral care compositions. Accordingly, while completely removing SLS from an oral care composition would help solve the stability of the catalyzing enzymes in the oral care formulation, there is desire to maintain SLS in oral care compositions for its foaming characteristics while improving the stability and efficacy of oral care composition including whitening agents and catalyzing enzymes.

The inventors have surprisingly develop a mixture of surfactants usable in the oral care composition that improves the stability of the catalyzing enzymes, the generation of the whitening enhancers, while maintaining or improving the foam characteristics of the oral care composition. In some implementations, these desired characteristics were observed even in formulation including high concentrations of SLS (up to 5 weight %). While not intending to be bound by theory, the inventors believe that the additional surfactants of the surfactant mixture are micelizing the SLS in a way that prevents it from interacting with the catalyzing enzymes. In some implementations, the oral care composition does not include more than 5 weight % SLS. In other implementations, the oral care composition does not include more than 2 weight % SLS The oral care composition of the present disclosure may include one or more catalyzing enzymes. The one or more enzymes include any enzyme capable of catalyzing a reaction between the one or more sources of hydrogen peroxide, or the hydrogen peroxide generated therefrom, and a suitable substrate, i.e., an acyl donor of the present disclosure, to generate a whitening enhancer, such as peracetic acid. Typically, the enzyme is a perhydrolyase. Perhydrolases are enzymes that generate peroxyacid via perhydrolysis. In enzyme-catalyzed perhydrolysis reactions, the acyl donor substrate (a peroxyacid precursor) is combined with a source of hydrogen peroxide and water. The perhydrolase catalyzes the formation of a peroxyacid, such as peracetic acid.

Enzymes having perhydrolytic activity include certain lipases, proteases, esterases, acyl transferases, aryl esterases, carbohydrate esterases, and combinations thereof. Examples include the perhydrolytic proteases disclosed in U.S. Pat. No. 7,510,859, which is herein incorporated by reference in its entirety, the perhydrolytic aryl esterases disclosed in U.S. Pat. No. 8,663,616, which is herein incorporated by reference in its entirety and the perhydrolytic aryl esterase/acyl transferase from *Mycobacterium smegmatis*, which is disclosed in U.S. Pat. No. 8,663,616. Typically, the perhydrolase is a perhydrolase carbohydrate esterase.

Even more typically, the perhydrolase carbohydrate esterase suitable for inclusion in the present oral care composition is a member of the carbohydrate esterase family 7 (CE-7). Enzymes from the CE-7 family are well known in the art (see Coutinho, P. M., Henrissat, B. "Carbohydrate-active enzymes: an integrated database approach" in Recent Advances in Carbohydrate Bioengineering, H. J. Gilbert, G. Davies, B. Henrissat and B. Svensson eds., (1999) The Royal Society of Chemistry, Cambridge, pp. 3-12, which is herein incorporated by reference in its entirety). The CE-7 family of enzymes has been demonstrated to be particularly effective for producing peroxyacids acids from a variety of acyl donor substrates when combined with a source of peroxygen, e.g., hydrogen peroxide (U.S. Pat. Nos. 7,794, 378; 7,951,566; 7,723,083; and 7,964,378 and U.S. Patent Application Publication Nos. 2008-0176299, 2010-0087529, 2011-0081693, and 2011-0236335 to DiCosimo et al.; each incorporated herein by reference in its entirety).

Members of the CE-7 family, which include, e.g., cephalosporin C deacetylases (CAHs; E.C. 3.1.1.41) and acetyl xylan esterases (AXEs; E.C. 3.1.1.72), share a conserved signature motif (Vincent et al., *J. Mol. Biol.*, 330:593-606 (2003), which is herein incorporated by reference in its entirety). The signature motif for CE-7 family members comprises three conserved motifs as follows (residue position numbering relative to reference sequence SEQ ID NO: 2; the CE-7 perhydrolase from *B. subtilis* ATCC® 31954™). The relative numbering accounts for small insertions or deletions (for example, typically five amino acids of less) within the aligned sequence.

The CE-7 signature motif includes: a) arginine ("Arg" or "R") at position 118, glycine ("Gly" or "G") at position 119 and glutamine ("Gln" or "Q") at position 120 of SEQ ID NO: 2; b) G at position 179, any amino acid ("XAA" or "X") at position 180, serine ("Ser" or "S") at position 181, Q at position 182 and G at position 183 of SEQ ID NO: 2; and c) histidine ("His" or "H") at position 298 and glutamic acid ("Glu" or "E") at position 299 of SEQ ID NO: 2.

Typically, the X at amino acid residue position 180 is glycine, alanine ("Ala" or "A"), proline ("Pro" or "P"), tryptophan ("Trp" or "W") or threonine ("Thr" or "T"). In some implementations, the X at amino acid residue position 180 is selected from the group consisting of glycine, alanine, proline, tryptophan, and threonine.

Further analysis of the conserved motifs within the CE-7 family indicates the presence of an additional conserved motif (Leucine ("Leu" or "L"), X and aspartic acid ("Asp" or "D"), i.e., LXD at amino acid positions 267-269 of SEQ ID NO: 2, that may be used to further define a perhydrolase belonging to the CE-7 carbohydrate esterase family. The X at amino acid residue position 268 is typically isoleucine ("Ile" or "I"), valine "Val" or "V" or methionine ("Met" or "M").

A number of well-known global alignment algorithms (i.e., sequence analysis software) may be used to align two or more amino acid sequences representing enzymes having perhydrolase activity to determine if the enzyme is comprised of the present signature motif. The aligned sequence(s) are compared to the reference sequence (SEQ ID NO: 2) to determine the existence of the signature motif.

In some implementations, a CLUSTAL alignment (such as CLUSTALW, e.g., version 1.83) using a reference amino acid sequence (as used herein the perhydrolase sequence, SEQ ID NO: 2) from the *Bacillus subtilis* ATCC® 31954™) is used to identify perhydrolases belonging to the CE-7 family. CLUSTAL is a series of widely used computer programs in bioinformatics for multiple sequence alignment and is described, for example, in Larkin et al., *Bioinformatics*, 2007 23(21): 2947-2948. doi:10.1093/bioinformatics/btm404, See also Higgins and Sharp, CABIOS, 5:151-153 (1989); Higgins et al., Nucleic Acids Res. 22:4673-4680 (1994); and Chema et al., Nucleic Acids Res 31 (13):3497-500 (2003)), which are each incorporated herein by reference in its entirety.

CLUSTAL (such as CLUSTALW, e.g., version 1.83 or CLUSTAL OMEGA e.g., version 1.2.3), is available from the European Molecular Biology Laboratory via the European Bioinformatics Institute. Suitable parameters for CLUSTALW or CLUSTAL OMEGA protein alignments include default parameters. Other suitable parameters for CLUSTAL W include GAP Existence penalty=15, GAP extension=0.2, matrix=Gonnet (e.g., Gonnet250), protein ENDGAP-1, protein GAPDIST=4, and KTUPLE=1. In some implementations, a fast or slow alignment is used with the default settings where a slow alignment is more desirable. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

Examples of other suitable algorithms that may be used to identify sequences comprising the present signature motif (when compared to the reference sequence) include, but are not limited to, Needleman and Wunsch (J. Mol. Biol. 48, 443-453 (1970); a global alignment tool) and Smith-Waterman (J. Mol. Biol. 147:195-197 (1981); a local alignment tool). In some implementations, a Smith-Waterman alignment is used with default parameters. An example of suitable default parameters include the use of a BLOSUM62 scoring matrix with GAP open penalty=10 and a GAP extension penalty=0.5.

Typically, the oral care composition of the present disclosure include one or more enzymes that comprise a CE-7 signature motif that aligns with SEQ ID NO: 2 using, e.g., CLUSTALW, the CE-7 signature motif comprising a) an RGQ motif at positions corresponding to positions 118-120 of SEQ ID NO: 2; b) a GXSQG (SEQ ID NO: 3) motif at positions corresponding to positions 179-183 of SEQ ID NO: 2 and a HE motif at positions corresponding to positions 298-299 of SEQ ID NO:2.

In some implementations, the enzyme used in the present oral care composition is a "CE-7 variant", i.e., a CE-7 perhydrolase having a genetic modification that results in at least one amino acid addition, deletion, and/or substitution when compared to the corresponding enzyme (typically a wild type CE enzyme) from which the variant was derived; so long as the CE-7 signature motif and the associated perhydrolytic activity are retained. Examples of CE-7 variants suitable for use in the present oral care composition are provided in U.S. Pat. No. 8,663,616, which is herein incorporated by reference in its entirety. A typical variant for use in the present oral care composition is SEQ ID NO: 1, wherein a serine is substituted for the cysteine present at position 277 in wild type *Thermotoga maritima* perhydrolase.

In some implementations, the perhydrolase of the present disclosure is a CE-7 variant comprising the CE-7 signature motif and having at least 33%, more typically at least 40%, more typically at least 42%, more typically at least 50%, more typically at least 60%, more typically at least 70%, more typically at least 80%, more typically at least 90%, and yet even more typically at least 90%, 91%, 92%, 93%, 94%, 95%, 96%, 97%, 98%, or 99% amino acid identity to SEQ ID NO: 1 (EZ-1) or SEQ ID NO: 2. In some implementations, the oral care composition of the present disclosure include an enzyme comprising an amino acid sequence having at least 80% amino acid sequence identity to SEQ ID NO:1. In other implementations, the oral care composition of the present disclosure includes an enzyme comprising the amino acid sequence of SEQ ID NO: 1.

As used herein the term "percent identity" refers to a relationship between two or more amino acid sequences (or polypeptide sequences, which is used interchangeably herein with the term "amino acid sequence") or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in: Biocomputing: Informatics and Genome Projects (Smith, D. W., ed.) Academic Press, NY (1993). Methods to determine identity are codified in publicly available computer programs, such as CLUSTALW or CLUSTAL OMEGA as described herein and as well known in the art.

The skilled artisan recognizes that variants of SEQ ID NO: 1, other CE-7 variants or SEQ ID NO: 2 (retaining the signature motifs) may also be obtained by hybridization. For example, variants of, e.g., SEQ ID NO: 1 may be identified by their ability to hybridize, under highly stringent conditions with the nucleic acid molecules associated with the amino acid sequence of SEQ ID NO: 1.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms.

Post-hybridization washes generally determine stringency conditions. Typically, the washing conditions include a series of washes starting with 6×SSC, 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. A more typical set of conditions uses higher temperatures in which the washes are identical to those above except for the temperature of the final two 30 minute washes in 0.2×SSC, 0.5% SDS was increased to 60° C. Another typical set of highly stringent hybridization conditions includes 0.1×SSC, 0.1% SDS, 65° C. and washed with 2×SSC, 0.1% SDS followed by a final wash 10, of 0.1% SSC, 0.1% SDS, 65° C.

In some implementations, variants of, e.g., SEQ ID NO: 1 comprising the above-identified CE-7 signature motifs, may be produced by mutagenesis. Various methods are known for mutating a nucleic acid sequence to produce a nucleic acid product with altered or enhanced activity including, but not limited to 1) random mutagenesis, 2) domain swapping (using zinc finger domains or restriction enzymes, 3) error-prone PCR (Melnikov at al., Nucleic Acids Research 27(4):1056-1062 (1999)); 4) site directed mutagenesis (Coombs at al., Proteins (1998), pp 259-311); and 5) "gene shuffling" (U.S. Pat. Nos. 5,605,793; 5,811, 238; 5,830,721; and 5,837,458, incorporated herein by reference). Proposed modifications are well within the routine skill in the art, as is determination of retention of biological activity of the encoded products.

In some implementations, the variants of, e.g., SEQ ID NO: 1 may demonstrate improved perhydrolysis activity in comparison to wild type enzymes or in comparison to SEQ ID NO: 1. Preparation of such variants may include, e.g., construction of an expression vector comprising the nucleotide sequence encoding a polypeptide that is structurally classified as a CE-7 enzyme or SEQ ID NO: 1, mutagenesis of the enzyme coding sequence, and finally isolation of variants with increased peroxyacid, such as peracetic acid, generation activity. Subsequent rounds of mutagenesis, if desired, allow for evolution of the enzyme-coding sequence. If desired, the regions of an enzyme important for enzymatic activity can be determined through routine site-directed mutagenesis, expression of the resulting variant polypeptides, and determination of their activities. Mutants may include deletions, insertions and point mutations, or combinations thereof.

The enzyme may have a particle size median diameter (D50) from about 10 µm to about 150 µm. For example, the particle size median diameter (D50) of the enzyme may be less than about 125 µm, less than about 65 µm, and/or less than about 50 µm. In other implementations, the enzyme may have a particle size median diameter (D50) from about 100 µm to about 300 µm. For example, the particle size median diameter (D50) of the enzyme may be about 50 µm, 100 µm, 125 µm, 130 µm, about 140 µm, about 150 µm, about 160 µm, about 170 µm, about 180 µm, about 190 µm, or about 200 µm to about 210 µm, about 220 µm, about 230 µm, about 240 µm, about 250 µm, about 260 µm, about 270 µm, about 280 µm, about 290 µm, or about 300 µm. In another example, the enzyme may have a particle size median diameter (D50) from about 100 µm to about 300 µm, about 110 µm to about 290 µm, about 120 µm to about 280 µm, about 130 µm to about 270 µm, about 140 µm to about 260 µm, about 150 µm to about 250 µm, about 160 µm to about 240 µm, about 170 µm to about 230 µm, about 180 µm to about 220 µm, or about 190 µm to about 210 µm.

The enzyme may be provided in the form of a powder, an enzyme powder, or a stabilized enzyme powder. Methods for making and stabilizing the enzyme powder are described in U.S. Patent Application Publication Nos. 2010-0086534 and 2010-0086535, the disclosures of which are incorporated herein by reference. The enzyme may be present in the enzyme powder in an amount of about 0.5 weight % to about 75 weight %, based on a dry weight of the enzyme powder. In a typical implementation, the enzyme may be present in the enzyme powder in an amount of about 10 weight % to about 50 weight %, or more typically in an amount of about 20 weight % to about 33 weight %, based on a dry weight of the enzyme powder.

The enzyme powder may include an excipient. The excipient may be or provide the balance of the enzyme powder. Accordingly, in at least one example, the enzyme powder may include only the enzyme and the excipient. In another example, the enzyme powder may include the enzyme, the excipient, and at least one additional component. The excipient may be an oligosaccharide having a number average molecular weight of at least about 1,250 and a weight average molecular weight of at least about 9,000. The oligosaccharide excipient may have a number average molecular weight of at least about 1,700 and a weight average molecular weight of at least about 15,000. Illustrative oligosaccharides may be or include, but are not limited to, maltodextrin, xylan, mannan, fucoidan, galactomannan, chitosan, raffinose, stachyose, pectin, insulin, levan, graminan, amylopectin, sucrose, lactulose, lactose, maltose, trehalose, cellobiose, nigerotriose, maltotriose, melezitose, maltotriulose, raffinose, kestose, and the like, and cominations or mixtures thereof. The oligosaccharides may also include, but are not limited to, water-soluble non-ionic cellulose ethers, such as hydroxymethyl-cellulose and hydroxypropylmethylcellulose, and mixtures thereof. The one or more excipients may be or include, but are not limited to, trehalose, lactose, sucrose, mannitol, sorbitol, glucose, cellobiose, α-cyclodextrin, carboxymethylcellulose, and the like, and combinations thereof. In a typical implementation, the oligosaccharide excipient is maltodextrin.

In one implementation, the catalyzing enzyme is provided in a suspension. For example, the catalyzing enzyme may be provide as a suspension of 60 weight % triacetin and 40 weight % spray-dried powder (maltodextrin containing 8 weight % perhydrolase enzyme), based on the total weight of the suspension. The amount of catalyzing enzyme in the oral care composition may be configured to provide from about 0.1 weight % to about 0.5 weight % catalyzing enzyme, based on the total weight of the oral care composition. In another implementation, the oral care composition includes from about 0.1 weight % to about 1.0 weight % catalyzing enzyme, from about 0.1 weight % to about 0.5 weight % catalyzing enzyme, and/or from about 0.1 weight % to about 2.5 weight % catalyzing enzyme. For example, the oral care composition may include 0.1 weight % catalyzing enzyme, 0.2 weight % catalyzing enzyme, or from about 0.1 weight % to about 0.2 weight % catalyzing enzyme, based on the total weight of the oral care composition.

In at least one implementation, the oral care composition may include a non-aqueous anhydrous liquid configured to control the viscosity thereof and/or suspend a component (e.g., solid) disposed or dispersed therein. Illustrative non-aqueous anhydrous liquids or viscosity control agents may be or include, but are not limited to, polypropylene glycol, materials containing propylene oxide groups, materials containing polyethylene oxide groups, polyoxyethylene-polyoxypropylene glycols, polysorbate 20 (TWEEN™ 20), POLOXAMER™ 124 (PLURONIC™ L44), polyethylene oxide-polypropylene oxide block copolymer having the formula $(EO)x(PO)y(EO)z$ with $x=11\pm3$, $z=11\pm3$ and $y=21\pm5$, POLOXAMER™ L35, POLOXAMER™ L31, polyethylene glycol 55 (PEG-55), glycerin, diethylene glycol, CREMOPHOR™ polyoxyethyleneglyceroltriricinoleat, GLUCAM™ P-10 propylene glycol ether of methyl glucose with 10 polypropylene oxide units, PLURIOL™ E300 alkoxylates based on ethylene oxide and propylene oxide, sodium cumene sulfonate (SCS), sodium xylene sulfonate (SXS), GLUCAM™ P-20 propylene glycol ether of methyl glucose with 20 polypropylene oxide units, GLUCAM™ E-20 ethylene glycol ether of methyl glucose with 20 polyethylene oxide units, GLUCAM™ E-10 ethylene glycol ether of methyl glucose with 10 polyethylene oxide units, and short chain ethoxylated propoxylated alcohols such as PPG2-Buteth-3, PPG3-Buteth-5, or PPG5-Buteth-7. Illustrative non-aqueous anhydrous liquids or viscosity control agents may also be or include, but are not limited to, Pluronic® L35, Pluronic® L43, Pluronic® L64, Pluronic® L10, Pluronic® L44, Pluronic® L62, Pluronic® 10R5, Pluronic® 17R4, Pluronic® L25R4, Pluronic® P84, Pluronic® P65, Pluronic® P104, Pluronic® P105, and the like, and combinations thereof, which are commercially available from BASF of Mount Olive, N.J. In a typical implementation, the non-aqueous anhydrous liquid is or includes a poly(ethylene glycol)-block-poly(propylene glycol)-block-poly(ethylene glycol) or PEG-PPG-PEG (PLURONIC® L-35).

In some implementations, the non-aqueous anhydrous liquid are configured to serve as a water-free humectant. In other implementations, the non-aqueous anhydrous liquid have a low molecular weight. For example, the non-aqueous anhydrous liquid may have a molecular weight of 5000 Daltons or less, 4000 Daltons or less, or 3000 Daltons or less. In one implementation, the non-aqueous anhydrous liquid has a molecular weight of 2000 Daltons or less.

In other implementations, the oral care composition includes additional non-aqueous anhydrous liquids. For example, the oral care composition may include one or more of polyethylene glycols, such as PEG400 and PEG600, or polyethylene/polypropylene glycol copolymers, such as PEG/PPG 38/8 and PEG/PPG-116/66.

The amount of the non-aqueous anhydrous liquid or viscosity control agents present in the oral care composition may vary widely. In at least one implementation, the amount of the non-aqueous anhydrous liquid or viscosity control agents present in the oral care composition may be from about 10 weight % to about 80 weight %, based on a total weight of the oral care composition. For example, the amount of the non-aqueous anhydrous liquid or viscosity control agents present in the oral care composition may be from about 10 weight %, about 15 weight %, about 20 weight %, about 25 weight %, about 30 weight %, about 35 weight %, about 40 weight %, about 45 weight %, about 50 weight %, about 55 weight %, or about 60 weight % to about 65 weight %, about 70 weight %, about 75 weight %, or about 80 weight %. In another example, the amount of the non-aqueous anhydrous liquid or viscosity control agents present in the oral care composition may be from about 40 weight % to about 80 weight %, about 42 weight % to about 78 weight %, about 44 weight % to about 76 weight %, about 46 weight % to about 74 weight %, about 48 weight % to about 72 weight %, about 50 weight % to about 70 weight %, about 52 weight % to about 68 weight %, about 54 weight % to about 66 weight %, about 56 weight % to about 62 weight %, or about 58 weight % to about 62 weight %. In yet another implementation, the amount of the non-aqueous anhydrous liquid or viscosity control agents present in the oral care composition may be greater than or equal to 40 weight %, greater than or equal to 42 weight %, greater than or equal to 44 weight %, greater than or equal to 46 weight %, greater than or equal to 48 weight %, greater than or equal to 50 weight %, greater than or equal to 52 weight %, greater than or equal to 53 weight %, greater than or equal to 54 weight %, greater than or equal to 66 weight %, greater than or equal to 68 weight %, or greater than or equal to 70 weight %.

In at least one implementation, the oral care composition may include one or more thickeners. The one or more thickeners may be any orally acceptable thickener or thickening agent. Illustrative thickeners may be or include, but are not limited to, colloidal silica, fumed silica, a cross-linked polyvinylpyrrolidone (PVP) polymer, cross-linked polyvinylpyrrolidone (PVP), and the like, and mixtures or combinations thereof. In a typical implementation, the one or more thickeners includes a cross-linked polyvinylpyrrolidone (PVP) polymer. In a more typical implementation, the one or more thickeners may be or include, but is not limited to, POLYPLASDONE™ XL-10, which is commercially available from Ashland Inc. of Covington, Ky.

In at least one implementation, the oral care composition may include additional and/or optional thickeners. Illustrative additional or optional thickeners may be or include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, and the like, and mixtures or combinations thereof.

In at least one implementation, the one or more thickeners may include a single thickener. For example, cross-linked polyvinylpyrrolidone (PVP) polymer. In another implementation, the one or more thickeners may include a plurality of thickeners. For example, cross-linked PVP polymer and a silica thickener. In another example, the one or more thickeners may include a plurality of silica thickeners.

The one or more thickeners may also include a polyvinylpyrrolidone-vinyl acetate copolymer (PVP-VA) (e.g., commercially available as Plasdone S-630 from Ashland Inc.), polyvinyl pyrrolidone-co-polyvinyl butyrate copolymer (PVP-VB), polyvinyl pyrrolidone-co-polyvinyl propionate copolymer, or mixtures thereof.

The amount or concentration of the one or more thickeners present in the oral care composition may vary widely. In at least one implementation, the amount of the one or more thickeners present in the oral care composition may from about 10 weight % to about 30 weight % based on the total weight of the oral care composition. For example, the amount of the one or more thickeners present in the oral care composition may be from about 10 weight %, about 11 weight %, about 12 weight %, about 13 weight %, about 14 weight %, about 15 weight %, about 16 weight %, about 17 weight %, about 18 weight %, about 19 weight %, about 20 weight %, or about 21 weight % to about 22 weight %, about 23 weight %, about 24 weight %, about 25 weight %, about 26 weight %, about 27 weight %, about 28 weight %, about 29 weight %, or about 30 weight %. In another example, the amount of the one or more thickeners present in the oral care composition may from about 12 weight % to about 30 weight %, about 13 weight % to about 29 weight %, about 14 weight % to about 28 weight %, about 15 weight % to about 27 weight %, about 16 weight % to about 26 weight %, about 17 weight % to about 25 weight %, about 18 weight % to about 24 weight %, about 19 weight % to about 23 weight %, or about 20 weight % to about 22 weight %. In a typical implementation, the amount of the one or more thickeners present in the oral care composition may be from about 20 weight % to about 22 weight %, more typically about 21 weight %.

However, in some implementations the oral care composition may not include additional thickeners. For example, in one implementation, the oral care composition does not include a thickener, such as PVP-VA.

In at least one implementation, the oral care composition does not include any encapsulations and/or film-type materials to enhance the stability thereof. For example, the oral care composition does not include any water-soluble or water-insoluble encapsulations and/or film-type materials configured to separate (e.g., physically) any one or more of the sources of hydrogen peroxide, the acyl donors, the non-aqueous anhydrous liquids, and/or the one or more thickeners from one another to thereby increase the stability of the oral care composition. In another example, the oral care composition does not include any polymeric encapsulations and/or film-type materials configured to separate (e.g., physically) any one or more of the sources of hydrogen peroxide, the acyl donors, the non-aqueous anhydrous liquids, and/or one or more thickeners from one another to thereby increase the stability of the oral care composition. Illustrative encapsulations may be or include, but are not limited to, nano-capsules or shells, micro-capsules or shells, macro-capsules or shells, micro-emulsions, nano-emulsions, or the like or combinations thereof.

As described above, the anhydrous matrix may form at least a portion of or be used in one or more oral care compositions. Illustrative oral care compositions may include, but are not limited to, a toothpaste (dentifrice), a prophylactic paste, a tooth powder, a tooth polish, a tooth gel (e.g., whitening gel), a chewing gum, a lozenge, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In a typical implementation, the anhydrous mixture may form at least a portion of or be used in a toothpaste. The anhydrous mixture may include or be combined with an orally acceptable vehicle to form the oral care composition. In an exemplary implementation, the orally acceptable vehicle may include glycerin.

The orally acceptable vehicle may include humectants, surface active agents, gelling agents, and the like, and combinations thereof. Illustrative humectants may be or include, but are not limited to, glycerin, propylene glycol, and the like, and combinations thereof. In at least one implementation, the humectant is present in an amount of from about 20 weight % to about 60 weight % based on a total weight of the oral care composition. In at least one implementation, the oral care composition is free or substantially free of polyol humectants. For example, the oral care composition does not contain any polyols as a humectant. In another implementation, the propylene glycol is present in an amount of from about 10 weight % to about 20 weight % based on a total weight of the oral care composition. In another implementation, the glycerin is present in an amount of from about 25 weight % to about 40 weight % based on a total weight of the oral care composition.

In at least one implementation, the components of the oral care composition may be combined with one another to provide a target viscosity. As used herein, the term "viscosity" may refer to the internal resistance to flow exhibited by a fluid (e.g., water) or the ratio of shearing stress to rate of shear, and may be measured in poise or centipoise (cP). The viscosity of the various compositions discussed and described herein may be determined using a Viscometer at a temperature of about 25° C. In at least one implementation, the viscosity or target viscosity of the oral care composition may be greater than or equal to about 10,000 cP and less than or equal to about 700,000 cP. For example, the viscosity or target viscosity of the oral care composition may be about 10,000 cP, about 15,000 cP, about 20,000 cP, about 25,000 cP, or about 30,000 cP to about 35,000 cP, about 40,000 cP, about 50,000 cP, about 75,000 cP, about 100,000 cP, about 120,000 cP, about 150,000 cP, about 175,000 cP, about 200,000 cP, about 300,000 cP, about 400,000 cP, about 500,000 cP, about 600,000 cP, or about 700,000 cP. In a typical implementation, the viscosity of the oral care composition is from about 30,000 cP to about 500,000 cP.

The oral care composition may include additional ingredients common to oral care products. Illustrative additional ingredients may include thickeners, flavoring agents, tartar control agents, sweeteners, humectants, colorants, dyes, and pigments. In some implementations, the oral care composition may include most orally acceptable additional ingredients common to oral care products. However, in some implementation, the orally acceptable additional ingredient must be selected in view of the requirement to maintain a non-aqueous or a substantially non-aqueous oral care composition. For example, in some implementations the additional ingredients will not affect the non-aqueous nature of the anhydrous matrix or the oral care composition based thereon.

In some implementations, the oral care composition includes an antioxidant. Acceptable antioxidants include BHA, BHT, vitamin A, carotenoids, vitamin E, flavonoids, polyphenols, ascorbic acid, herbal antioxidants, chlorophyll, melatonin and mixtures thereof. In some implementations, the oral care composition includes from about 0.001% to about 1% antioxidants based on a total weight of the oral care composition. In one implementation, the oral care composition includes about 0.03% antioxidant by weight.

According to one implementation, the oral care composition includes one or more flavoring agent. Useful flavoring agents include any material or mixture of materials operable to enhance the taste of the oral care composition. Any orally acceptable natural or synthetic flavoring agent can be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA) and mixtures thereof.

In some implementations, the oral care composition includes from about 0.01% to about 5% flavoring agents based on a total weight of the oral care composition. In another implementation, the oral care composition includes from about 0.05% to about 2% flavoring agents. In yet another implementation, the oral care composition includes from about 0.1% to about 3%, from about 0.2% to about 2.5%, or about 1.5% flavoring agents based on a total weight of the oral care composition. For example, the oral care composition may include about 1.5% of dental cream flavor.

In some implementations, the oral care composition may also include one or more sweeteners. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Some implementations may include one or more sweeteners. In some implementations, the oral care composition includes from about 0.005% to about 5% sweeteners based on a total weight of oral care composition. In other implementations, the oral care composition includes from about 0.01% to about 1% sweeteners. For example, the oral care composition may include about 0.5% sodium saccharin and about 0.04% sucralose.

In some implementations, the oral care composition may also include one or more pH modifying agents. The pH modifying agents among those useful herein include acidifying agents to lower pH, basifying agents to raise pH and buffering agents to control pH within a desired range. For example, one or more compounds selected from acidifying, basifying and buffering agents can be included to provide a pH of 2 to 10, or in various implementations from about 2 to about 8, from about 3 to about 9, from about 4 to about 8, from about 5 to about 7, from about 6 to about 10, and from about 7 to about 9. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range. In some implementations, the oral care composition includes from about 0.01% to about 10% pH modifier agents based on a total weight of the oral care composition. For example, the oral care composition may include about 0.9% sodium acid pyrophosphate (SAPP) and about 2% tetrasodium pyrophosphate (TSPP) as a pH modifier.

In some implementations, the oral care composition may include colorants. Colorants, such as dyes or pigments, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

The oral care composition may also include one or more other active ingredients, which are operable for the prevention or treatment of a condition or disorder of hard or soft tissue of the oral cavity, the prevention or treatment of a physiological disorder or condition, or to provide a cosmetic benefit.

Some implementations of the present disclosure include a dental abrasive or combination of dental abrasive agents. As used herein, the term "abrasive" or "abrasive agent" also includes materials commonly referred to as "polishing agents." Any orally acceptable abrasive can be used, but typically, type, fineness (particle size) and amount of abrasive should be selected so that tooth enamel is not excessively abraded in normal use of the composition. Suitable abrasives include without limitation silica (in the form of silica gel, hydrated silica or precipitated silica), alumina, insoluble phosphates, calcium carbonate, resinous abrasives such as urea-formaldehyde condensation products and the like.

Among insoluble phosphates useful as abrasives are orthophosphates, polymetaphosphates and pyrophosphates. Illustrative examples are dicalcium orthophosphate dihydrate, calcium pyrophosphate, n-calcium pyrophosphate, tricalcium phosphate, calcium polymetaphosphate and insoluble sodium polymetaphosphate.

Average particle size of an abrasive, if present, is generally from about 0.1 to 100 about μm. For example, in one implementation, the particle size is from about 1 to about 80 μm or from about 5 to about 60 μm. In some implementations, one or more abrasives are present in an amount of from about 0.01% to about 70% by weight, based on the total weight of the oral care composition. In other implementations, the oral care composition includes from about 0.1% to about 60% abrasives. In some implementations, the abrasive is calcium pyrophosphate. In some implementations, the oral care composition includes from 0.01% to about 70% calcium pyrophosphate based on a total weight of the oral care composition. In another implementation, the oral care composition includes about 20% calcium pyrophosphate.

In various implementations of the present disclosure, the oral care composition includes an anticalculus agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some implementations, the anticalculus agent is present in an amount of from about 0.01% to about 30% weight based on the total weight of the oral care composition. In some implementations, the oral care composition includes a mixture of anticalculus agents. In some implementations, tetrasodium pyrophosphate (TSPP) and sodium tripolyphosphate (STPP) are used as the anticalculus agents. In some implementations, the anticalculus agent includes from 0.1% to 10% TSPP, or about 2% TSPP.

Another component of the present compositions may be a synthetic anionic polymeric polycarboxylate, which acts as a stabilizer for the polyphosphate anti-tartar agent and which may help to block access of painful or pain-causing materials, such as sugars, to the tooth nerves.

In some implementations, the oral care composition optionally includes a source of fluoride ions. In some implementations, the source of fluoride ions is selected from: fluoride, monofluorophosphate (MFP), and fluorosilicate salts. In some implementations, one or more fluoride ion-releasing compounds are optionally present in an amount providing a total of 100 to 20,000 ppm, 200 to 5,000 ppm, or 500 to 2,500 ppm, fluoride ions. If present, in some implementations, the amount of fluoride source in the oral care composition ranges from about 0.01% to about 10% by weight, based on the total weight of the oral care composition, typically about 1.1%. For example, in one implementation, the oral care composition may include about 0.76% MFP.

The oral care composition may also include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. In some implementations, one or more stannous ion sources are included in the oral care composition. For example, the oral care composition may include from about 0.01% to about 10% stannous ion source by weight, based on the total weight of the oral care composition. In one implementation, the oral care composition includes from about 0.1% to about 7% stannous ion source or from about 0.2% to about 5% stannous ion source.

In one or more implementations, the present disclosure may provide methods for whitening teeth in a human or animal subject with an oral care composition. As used herein "animal subject" may include higher order non-human mammals such as canines, felines, and horses. The method may include contacting the oral care composition thereof with water. For example, the method may include contacting the source of hydrogen peroxide of the oral care composition with water to initiate the formation of hydrogen peroxide. The method may also include generating the whitening enhancer (e.g., peracetic acid) within less than 2 min, less than 1.5 min, or less than 1 min. The method may also include contacting the surface of the teeth with the oral care composition and/or the whitening enhancer generated from the enzyme-catalyzed perhydrolysis of the source of hydrogen peroxide and the acyl donor. Contacting the surface of the teeth with the oral care composition may include brushing the teeth with the oral care composition. Contacting the surface of the teeth with the oral care composition may also include disposing the oral care composition in a dental tray (e.g., reservoir of the dental tray) and disposing the dental tray about the teeth. The dental tray may be applied to the teeth and left for at least 5 minutes, typically at least 10 minutes, or more typically at least 30 minutes. After each treatment with the oral care composition the teeth may be treated with a tooth desensitizing formulation. Illustrative desensitizing formulations may contain potassium nitrate, citric acid, citric acid salts, strontium chloride and the like.

In at least one implementation, the oral care composition may be applied and/or contacted with the surfaces of the teeth at predetermined intervals. For example, a daily basis, at least once a day for multiple days, or alternatively every other day. In another example, the oral care composition thereof may be applied and/or contacted with the surfaces of the teeth at least once a day, at least once every two days, at least once every three days, at least once every five days, at least once a week, at least once every two weeks, or at least once a month. The oral care composition may be utilized for up to 2 weeks, up to 3 weeks, up to 4 weeks, up to 6 weeks, up to 8 weeks, or greater.

The dental tray may be of any conventional form, and may be formed from conventionally used polymers, such as thermoplastic polymers. Thermoset polymers also may be used. Accordingly, the dental tray may range from highly flexible to a low flexibility. The thermoplastic polymers are typical, and those that may be used include, but are not limited to, polyethylene and polypropylene polymers, their derivatives and copolymers, silicone elastomers, polyurethanes and derivatives, polycaprolactams, polystyrene and derivatives, polybutadiene and derivatives, polyisoprene and derivatives, and polymethacrylate and its derivatives, and the like, and combinations thereof.

In at least one implementation, the present disclosure may provide a method for increasing the stability of one or more enzymes in an anhydrous mixture and/or an oral care composition based thereon. For example, the present disclosure may provide a method for maintaining the viability of the enzyme for an extended period of time under accelerated aging conditions. The method may include combining, mixing, suspending, or otherwise contacting the enzyme with the anhydrous matrix to form the oral care composition. The oral care composition, including the enzyme and the anhydrous matrix may be combined with one another in a single, homogenous phase.

In some implementations, the oral care composition provides increased stability for the enzymes in the oral care products without encapsulations and/or film-type materials to enhance the stability thereof. The present inventors have also surprisingly and unexpectedly discovered that the oral care composition maintains the stability of the enzyme in the oral care composition for at least 8 weeks, at least 12 weeks, at least 13 weeks, or greater, when exposed to accelerated aging conditions.

As used herein, "stability," "increased stability," and/or "high stability" may refer to an oral care composition where the amount or concentration of the source of hydrogen peroxide or the hydrogen peroxide thereof is not reduced by more than 15%, more than 18%, more than 20%, more than 25%, or more than 30% over a period of at least 8 weeks, at least 10 weeks, at least 12 weeks, at least 13 weeks, or greater, when aged at a temperature of at least 40° C. and/or at about 75% relative humidity (RH). For example, a stable oral care composition or an oral care composition having "stability," "increased stability," and/or "high stability" may refer to an oral care composition including the anhydrous matrix and the one or more catalyzing enzymes, typically in a single phase, where the amount of hydrogen peroxide in the source of hydrogen peroxide of the oral care composition is not reduced by more than 15%, more than 18%, more than 20%, more than 25%, or more than 30% over a period of at least 8 weeks, at least 10 weeks, at least 12 weeks, at least 13 weeks, or greater, when aged at a temperature of at least 40° C. and 75% RH.

As discussed above, the one or more catalyzing enzymes may be configured to catalyze a reaction between the one or more sources of hydrogen peroxide, or the hydrogen peroxide thereof, and the one or more acyl donors to generate a whitening enhancer. For example, a catalyzing enzyme may be configured to catalyze a reaction between the one or more acyl donors and the hydrogen peroxide released from the sources of hydrogen peroxide to generate the whitening enhancer. In at least one implementation, the whitening enhancer is peroxyacid or peracetic acid.

The amount or concentration of the peracetic acid generated by perhydrolysis may vary widely. In at least one implementation, the amount of the peracetic acid generated may be from about 0.1 ppm to about 10,000 ppm based on a total weight of the oral care composition. For example, the amount of the peracetic acid generated may be from about 0.1 ppm, about 0.5 ppm, about 1 ppm, about 5 ppm, about 10 ppm, about 15 ppm, about 20 ppm, about 50 ppm, about 100 ppm, about 150 ppm, about 200 ppm, about 300 ppm, about 500 ppm, about 600 ppm, about 700 ppm, about 800 ppm, or about 900 ppm to about 1,000 ppm, about 1,200 ppm, about 1,400 ppm, about 1,600 ppm, about 1,800 ppm, about 2,000 ppm, about 2,500 ppm, about 3,000 ppm, about 3,500 ppm, about 4,000 ppm, about 5,000 ppm, about 6,000 ppm, about 7,000 ppm, about 8,000 ppm, about 9,000 ppm, or about 10,000 ppm. In another example, the amount of the peracetic acid generated may be less than 0.1 ppm, less than 0.5 ppm, less than 1 ppm, less than 5 ppm, less than 10 ppm, less than 15 ppm, less than 20 ppm, less than 50 ppm, less than 100 ppm, less than 150 ppm, less than 200 ppm, less than 300 ppm, less than 500 ppm, less than 600 ppm, less than 700 ppm, less than 800 ppm, less than 900 ppm, less than 1,000 ppm, less than 1,200 ppm, less than 1,400 ppm, less than 1,600 ppm, less than 1,800 ppm, less than 2,000 ppm, less than 2,500 ppm, less than 3,000 ppm, less than 3,500 ppm, less than 4,000 ppm, less than 5,000 ppm, less than 6,000 ppm, less than 7,000 ppm, less than 8,000 ppm, less than 9,000 ppm, or less than 10,000 ppm. In a typical implementation, the amount of the peracetic acid generated is less than 2000 ppm based on a total weight of the oral care composition.

In at least one implementation, the generation of the whitening enhancer from the oral care composition may be initiated by contact with water. For example, contacting the oral care composition with water may initiate perhydrolysis to thereby generate the whitening enhancer. In another implementation, the generation of the whitening enhancer from the oral care composition may be initiated by contact with a surface of the oral cavity. For example, contacting the oral care composition with a surface of the oral cavity, or the saliva thereof, may initiate perhydrolysis to thereby generate the whitening enhancer.

In at least one implementation, the whitening enhancer of the oral care composition may be generated within at least 3 minutes (min) from contacting the oral care composition with water or initiation of the perhydrolysis reaction. For example, the whitening enhancer of the oral care composition may be generated in less than or equal to 3 min, less than or equal to 2.8 min, less than or equal to 2.6 min, less than or equal to 2.4 min, less than or equal to 2.2 min, less than or equal to 2.0 min, less than or equal to 1.8 min, less than or equal to 1.6 min, less than or equal to 1.4 min, less than or equal to 1.2 min, less than or equal to 1.0 min, less than or equal to 0.8 min, less than or equal to 0.6 min, or less than or equal to 0.4 min. In a typical implementation, the whitening enhancer is generated within two minutes from contacting the oral care composition with water.

The present disclosure may also provide a method for the in situ generation of a whitening enhancer, such as peracetic acid. The method may include admixing, stirring, or otherwise contacting the oral care composition, including the anhydrous matrix and the enzyme, with water (e.g., added water and/or water of the oral cavity). The method may also include contacting the source of hydrogen peroxide with water to initiate the formation of hydrogen peroxide.

EXAMPLES

Aspects of the present disclosure may be further understood by referring to the following examples. The examples are illustrative, and are not intended to be limiting embodiments thereof.

Table 1 illustrates two oral care compositions using surfactant mixtures according to implementations of the present disclosure. Table 1 also illustrates a comparative compositions using the same ingredients as the oral care composition but only SLS as the surfactant.

TABLE 1

| Ingredient | Oral Care Composition #1 Weight % | Oral Care Composition #2 Weight % | Comparative Composition Weight % |
|---|---|---|---|
| Catalyzing Enzyme Suspension * | 1.25 | 1.26 | 1.25 |
| Source of Hydrogen Peroxide (18% Hydrogen Peroxide) ** | 0.55 | 0.55 | 0.55 |
| Acyl Donor | 13.0 | 12.23 | 17.5 |
| PVP-VA | 6.00 | 6.00 | 6.00 |
| Poloxamer L35 | 15.6 | 13.0 | 23.1 |
| xPVP | 16.0 | 13.0 | 16.0 |
| Sodium Monofluorophosphate | 0.76 | 0.76 | 0.76 |
| Sodium Saccharin | 0.60 | 0.60 | 0.60 |
| Sucralose | 0.05 | 0.05 | 0.05 |
| Calcium Pyrophosphate | 25.0 | 25.0 | 15.0 |
| Fumed Silica | 2.00 | 2.00 | 2.00 |
| Flavorant | 2.25 | 2.25 | 2.25 |

TABLE 1-continued

| Ingredient | Oral Care Composition #1 Weight % | Oral Care Composition #2 Weight % | Comparative Composition Weight % |
|---|---|---|---|
| PEG 600 | 10.0 | 10.0 | 10.0 |
| Sodium Lauryl Sulfate | 2.00 | 1.20 | 2.00 |
| Anhydrous Cocamidopropyl Betaine | 2.00 | 1.10 | — |
| Poloxamer L1220 | 6.00 | 7.70 | — |
| Sodium Acid Pyrophosphate | 0.90 | 0.90 | 0.90 |
| Tetrasodium Pyrophosphate | 2.00 | 2.00 | 2.00 |
| Butylated Hydroxytoluene | 0.04 | 0.40 | 0.04 |
| Total | 100.00 | 100.00 | 100.00 |

* 1.25-1.26 weight % of the Enzyme Suspension contains 0.2 weight % of catalyzing enzyme in the final oral care composition.
** 0.55 wt. % of PVP-HP contains 0.1 wt. % hydrogen peroxide in the final oral care composition.

The stability of Oral Care Compositions 1-2 as well as the Comparative Composition were evaluated under accelerated aging conditions. In particular, each of the compositions were aged in an incubator maintained at 40° C. and 75% Relative Humidity (RH) for 13 weeks. The stability of each composition (Oral Care Composition #1, Oral Care Composition #2, and the Comparative Composition) was evaluated by determining the amount of hydrogen peroxide (HP) contained in each of the compositions before and after exposure to accelerated aging conditions for 13 weeks. The amount of HP contained in each of the compositions was determined via active titration (i.e., Iodometric Titration). Particularly, about 1.3 g of each composition was measured in respective beakers. 25 ml of glacial acetic acid was then added to each of the beakers, followed by 50 ml of an ethanol/water (1:1 v/v) solution. The resulting solution was stirred or agitated until a paste/gel was fully suspended from the mixture. Then, 5 ml of a 20 wt. % potassium iodide solution and four drops of an ammonium molybdate solution/catalyst were added, and the resulting mixture was mixed for 5 minutes (min), resulting in a yellow or yellow tinted solution. 2 ml of a starch indicator was then added to each of the yellow solutions, thereby turning the yellow solution brown in color. The brown solution/mixture was then titrated with a 0.1 N sodium thiosulfate solution until the brown color dissipated, leaving a clear solution. The amount (ml) of the sodium thiosulfate solution used was then recorded and used to determine the amount of HP (wt. %) in each of the compositions. The results of the active titration are summarized in Table 2.

TABLE 2

| | Initial Concentration (theoretical) At 25° C. | 4 weeks at 40° C. | 8 weeks at 40° C. | 13 weeks at 40° C. |
|---|---|---|---|---|
| Comparative Composition | 0.1 | 0.12 | 0.1 | 0.09 |
| Oral Care Composition #1 | 0.1 | 0.07 | 0.07 | 0.07 |
| Oral Care Composition #2 | 0.1 | 0.1 | 0.09 | 0.08 |

As illustrated in Table 2, after exposure to accelerated aging conditions, Oral Care Composition #1 and Oral Care Composition #2 better maintained stability relative to the Comparative Composition. In particular, Oral Care Composition #1 showed no loss of HP over 13 weeks of accelerated aging conditions, and Oral Care Composition #2 showed a 20% loss of HP over the 13 weeks of accelerated aging conditions compared to the 25% HP loss of the Comparative Composition.

The amount of a whitening enhancer, i.e., peracetic acid (PAA), being generated from each of the composition (Oral Care Composition #1, Oral Care Composition #2, and the Comparative Composition) of Table 1 was also evaluated. In particular, the PAA generation after accelerated aging conditions as described above were evaluated as an indicator of stability. The generation of PAA generated from each of the compositions was evaluated via HPLC and UV/Vis. Since PAA is not visible via UV-Vis, secondary compounds that are visible or absorb in the UV-Vis spectrum were derived from the generated PAA via successive oxidation reactions. To derive the secondary compounds, about 0.5 g of each of the compositions was mixed with 0.5 g of a phosphate buffer solution (pH=7.0) for two minutes. 360 µl of the resulting solution/mixture were then transferred to a microfuge tube containing 40 µl of 1.3 M phosphoric acid and mixed or agitated to reach a final pH of less than 3, thereby terminating the enzymatic reaction. 100 µl of clarified supernatant was then transferred to an HPLC container/vial containing 300 µl of water and 100 µl of a methyl tolyl sulfide (MTS) reagent, and mixed or agitated in the dark for at least 10 min, thereby reacting the PAA with the MTS reagent to produce methyl tolyl sulfoxide (MTSO) and acetic acid (AcOH). Then 400 µl of acetonitrile and 100 µl of a triphenyl phosphine (TPP) reagent was added to the solution and allowed to react in the dark for 30 min. After 30 min, 100 µl of acetonitrile was added and mixed thoroughly, and the resulting solution was analyzed via HPLC. The calculated concentration of MTSO was then corrected for dilution (i.e., during the acid quench step), concentration (i.e., during the centrifugation step), and total reaction volume. It should be appreciated that the concentration of PAA is equivalent to the calculated concentration of MTSO including the aforementioned corrections. The amount of PAA generated from each of the compositions of Table 1 is summarized in Table 3.

TABLE 3

|  | Initial PAA value (theoretical) | 4 weeks at 40° C. | 8 weeks at 40° C. | 13 weeks at 40° C. |
| --- | --- | --- | --- | --- |
| Comparative Composition | 800 | N/A | 378 | 200 |
| Oral Care Composition #1 | 800 | 505 | 454 | 583 |
| Oral Care Composition #2 | 800 | 816 | 621 | 629 |

As illustrated in Table 3, PAA was successfully generated in situ after a matter of seconds after exposure to accelerated aging conditions. For comparison purposes, a concentration greater than 300 is considered a good result. The generation of the PAA in situ indicates that the catalyzing enzyme was still active after exposure to accelerated aging conditions. However, as illustrated in Table 3, the Comparative Composition displayed a dramatic decrease in the amount of PAA generated after 13 weeks. The amount of PAA generated decreased by 75% over the 13 weeks of accelerated aging. In contrast, Oral Care Compositions #1 and #2 showed only about 25% decrease in the amount of PAA generated over the 13 weeks of accelerated aging.

It should be appreciated that about 500 ppm of PAA may be generally equivalent to conventional oral care products (e.g., dentifrices) containing 1% HP. For example, the performance of 500 ppm of PAA is generally equivalent to a toothpaste or other oral care product containing 1% HP. Accordingly, it should be appreciated that oral care products incorporating or including the combination of 0.1 wt. % HP and 0.1% catalyzing enzyme may exhibit relatively improved whitening efficacy as compared to oral care products including 1% HP.

As illustrated in Tables 2 and 3, the oral care compositions of the present disclosure display good stability in terms of both loss of HP and decrease in PAA generation.

The amount of foam generated during brushing may impact the desirability of an oral care composition by consumers. Accordingly, it may be desirable for oral care compositions to have an acceptable foaming capability, especially as compared to other commercially available products. The foaming capability for the compositions of Table 1 were evaluated using a SITA foam tester and by recording the foam volume generated after 30 seconds as follows: testing samples for each of the compositions of Table 1 were prepared at a 1:4 ratio by suspending 200 grams of the composition in 800 grams of deionized water. The samples were then added to the SITA foam tester and data was recorded while spinning at 200 rpms. The results after 30 seconds of spinning are summarized in Table 4.

TABLE 4

|  | Foam Volume (mL) |
| --- | --- |
| Comparative Composition | 210 |
| Oral Care Composition #1 | 208 |
| Oral Care Composition #2 | 222 |

While foaming levels are usually correlated to the amount of SLS in a composition, as illustrated in Table 4, Oral Care Composition #2 (1.2% SLS) displayed an improved foaming capability over the Comparative Composition (2% SLS). This is particularly significant as it has been previously considered a challenge to maintain acceptable foaming levels with lower amounts of SLS. However, as illustrated in Table 4, the novel oral care composition of the present disclosure maintains acceptable foaming levels even when the amount of SLS is half of the standard 2% used in conventional comparative products.

In order to evaluate the whitening efficacy of the oral care compositions according to the present disclosure, an in vitro brushing study of Oral Care Composition #2, the Comparative Composition, and a commercial/conventional whitening toothpaste containing 0.1% hydrogen peroxide was conducted. Particularly, artificially stained bovine incisors individually mounted to resin blocks were obtained from Therametric Technologies, Inc. The teeth had L* value above 58 and below 64. All measurements were taken using a handheld spectrophotometer. Heads of manual toothbrushes were removed from their handles and mounted on a brushing assembly/machine. 1:1 slurries of the dentifrice to artificial saliva (2 g of dentifrice and 2 g of artificial saliva) were prepared using samples of Oral Care Composition #2, the Comparative Composition, and the commercial/conventional whitening toothpaste. The slurries were freshly prepared for each individual treatment. The teeth were brushed for a total of 2 minutes with 250 grams of pressure at a rate of 120 strokes per minute. After brushing was terminated, the slurry was removed, and residual toothpaste was rinsed away with 100 grams of deionized water. The teeth were then gently blotted with a paper towel to remove any excess liquids and measurements were taken with the spectrophotometer. The brushing treatment and measurement cycle was repeated a total of 14 times to mimic twice daily use of each product for 7 days.

The L*, a*, b* values after treatment were compared to the baseline values to calculate the change in the whiteness of each of the teeth. The change in whiteness index (ΔW*) is summarized in Table 5. It should be appreciated that the whiteness index (W*) is a measure of overall color change relative to pure white, and is given by formula (5), and the change in whiteness index (ΔW*) is measured by formula (6). It should further be appreciated that the more negative the value of ΔW*, the closer the tooth color is to white.

$$W^* = ((L^*-100)^2 + (a^*)^2 + (b^*)^2)^{1/2} \qquad (5)$$

$$\Delta W^* = W^*\text{treated} - W^*\text{baseline} \qquad (6)$$

TABLE 6

| | | Number of Brushing Treatments | | | | | | |
|---|---|---|---|---|---|---|---|---|
| | | 0 | 1 | 2 | 3 | 4 | 5 | 6 | 7 |
| 0.1% HP Dentifrice | ΔW* | 0 | −1.10 | −1.50 | −2.69 | −3.60 | −3.97 | −4.42 | −4.94 |
| Comparative Composition | ΔW* | 0 | −5.80 | −7.83 | −8.77 | −9.75 | −10.27 | −11.00 | −10.91 |
| Oral Care Composition #2 | ΔW* | 0 | −9.66 | −11.87 | −13.83 | −14.00 | −14.77 | −14.67 | −15.10 |

As illustrated in Table 6, Oral Care Composition #2 provided improved whitening effect as compared to both a conventional dentifrice having 0.1% HP and a Comparative Composition using only SLS as the surfactant. As illustrated in Table 6, the oral care compositions of the present disclosure have enhanced whitening efficacy due the improved HP stability and PAA generation, in addition to the catalyzing enzyme stability effects provided by the surfactant mixture over SLS.

---

What is claimed is:

1. An oral care composition, comprising:
a catalyzing enzyme; and
an anhydrous matrix configured to at least partially stabilize the catalyzing enzyme, wherein the anhydrous matrix comprises:
 a source of hydrogen peroxide;
 an acyl donor;
 a non-aqueous anhydrous liquid; and
 a surfactant mixture,
 wherein the surfactant mixture comprises sodium lauryl sulfate (SLS), Betaine, and a poloxamer having a molecular weight of 5,000 or more Daltons.

2. The oral care composition of claim 1, wherein the poloxamer in the surfactant mixture is at least one of an ethylene oxide-propylene oxide polymer or a polyethylene glycol/polypropylene glycol (PEG/PPG) copolymer, and wherein the betaine is anhydrous cocamidopropyl betaine.

3. The oral care composition of claim 2, wherein the surfactant mixture comprises:
from about 0.5 weight % to about 5.0 weight % SLS, based on a total weight of the oral care composition;
from about 0.01 weight % to about 5.0 weight % anhydrous cocamidopropyl betaine, based on the total weight of the oral care composition; and
from about 0.5 weight % to about 20.0 weight % of the PEG/PPG copolymer, based on the total weight of the oral care composition.

4. The oral care composition of claim 2, wherein the surfactant mixture comprises:
from about 0.5 weight % to about 3.0 weight % SLS, based on a total weight of the oral care composition;
from about 0.5 weight % to about 3.0 weight % anhydrous cocamidopropyl betaine, based on the total weight of the oral care composition; and
from about 2.0 weight % to about 10.0 weight % of the PEG/PPG copolymer, based on the total weight of the oral care composition.

5. The oral care composition of claim 2, wherein the surfactant mixture consists essentially of:
from about 1.0 weight % to about 2.0 weight % SLS, based on a total weight of the oral care composition;
from about 1.0 weight % to about 2.0 weight % anhydrous cocamidopropyl betaine, based on the total weight of the oral care composition; and
from about 3.0 weight % to about 8.0 weight % of the PEG/PPG copolymer, based on the total weight of the oral care composition.

6. The oral care composition of claim 1, wherein the catalyzing enzyme has perhydrolytic activity and is capable of generating peracetic acid via enzyme-catalyzed perhydrolysis.

7. The oral care composition of claim 1, wherein the source of hydrogen peroxide is a cross-linked polyvinylpyrrolidone (PVP) hydrogen peroxide complex.

8. The oral care composition of claim 1, wherein the anhydrous matrix is substantially free of water.

9. The oral care composition of claim 1, wherein the acyl donor is one or more of a $C_{2-18}$ carboxylic acid, a hydrolysable ester, and mixtures thereof.

10. The oral care composition of claim 1, wherein the acyl donor is triacetin.

11. The oral care composition of claim 1, further comprising a thickener, wherein the thickener comprises a cross-linked polyvinylpyrrolidone.

12. The oral care composition of claim 11, wherein the thickener further comprises a silica thickener.

13. The oral care composition of claim 1, wherein the catalyzing enzyme comprises a CE-7 signature motif that aligns with SEQ ID NO: 2, the CE-7 signature motif comprising a) an RGQ motif at positions corresponding to positions 118-120 of SEQ ID NO: 2; b) a GXSQG (SEQ ID NO: 3) motif at positions corresponding to positions 179-183 of SEQ ID NO: 2 and an HE motif at positions corresponding to positions 298-299 of SEQ ID NO:2.

14. The oral care composition of claim 1, wherein the catalyzing enzyme comprises an amino acid sequence comprising a CE-7 signature motif and having at least 80% amino acid sequence identity to SEQ ID NO:1.

15. The oral care composition of claim 1, wherein the non-aqueous anhydrous liquid comprises a polyethylene oxide-polypropylene oxide block copolymer having a molecular weight of 5,000 Daltons or less.

16. The oral care composition of claim 15, wherein the non-aqueous anhydrous liquid comprises poly(ethylene glycol)-block-poly(propylene glycol)-block-poly(ethylene glycol).

17. The oral care composition of claim 1, wherein the catalyzing enzyme comprises SEQ ID NO:1.

18. A method for whitening teeth, comprising contacting the oral care composition of claim 1 with water on a surface of the teeth, wherein contacting the oral care composition with water on the surface of the teeth generates peracetic acid.

* * * * *